(12) United States Patent
Allmendinger

(10) Patent No.: US 8,537,969 B2
(45) Date of Patent: Sep. 17, 2013

(54) APPARATUS FOR SPECIFYING THE QUANTITY OF A CONTRAST MEDIUM IN THE CONTEXT OF MEDICAL IMAGING

(75) Inventor: Thomas Allmendinger, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 79 days.

(21) Appl. No.: 13/277,245

(22) Filed: Oct. 20, 2011

(65) Prior Publication Data

US 2012/0101376 A1 Apr. 26, 2012

(30) Foreign Application Priority Data

Oct. 26, 2010 (DE) .......................... 10 2010 042 931

(51) Int. Cl.
*G01N 23/04* (2006.01)

(52) U.S. Cl.
USPC .................................. 378/62; 378/5; 600/431

(58) Field of Classification Search
USPC ..................... 600/407–431; 378/5–8, 62–68, 378/98–98.12
See application file for complete search history.

(56) References Cited

U.S. PATENT DOCUMENTS

| 7,551,721 B2* | 6/2009 | Nakaura et al. ............. 378/98.12 |
| 7,668,290 B2* | 2/2010 | Tanaka ............................. 378/62 |
| 7,672,711 B2* | 3/2010 | Haras et al. ..................... 600/431 |
| 7,756,324 B2* | 7/2010 | Ohishi ............................ 382/154 |
| 2006/0132483 A1* | 6/2006 | Ohishi ............................ 345/419 |
| 2006/0224104 A1 | 10/2006 | Ohishi et al. |
| 2007/0066892 A1* | 3/2007 | Haras et al. ..................... 600/425 |
| 2007/0195932 A1* | 8/2007 | Nakaura et al. ............. 378/98.12 |
| 2008/0027309 A1 | 1/2008 | Hempel et al. |
| 2008/0232548 A1* | 9/2008 | Tanaka .......................... 378/98.2 |
| 2008/0253503 A1* | 10/2008 | Proksa ............................. 378/5 |
| 2010/0183207 A1* | 7/2010 | Sakaguchi et al. ............. 382/128 |
| 2011/0313287 A1 | 12/2011 | Komatsu et al. |

FOREIGN PATENT DOCUMENTS

| DE | 102006032991 A1 | 1/2008 |
| JP | 2006305323 A | 11/2006 |
| JP | 2006325615 A | 12/2006 |
| WO | WO 2009012023 A1 | 1/2009 |
| WO | WO 2010101184 A1 | 9/2010 |

OTHER PUBLICATIONS

German Office Action for German Application No. DE 10 2010 042 931.7 dated Jun. 24, 2011.
German Priority document for German Application No. DE 10 2010 042 931.7 (Not Yet Published).

* cited by examiner

*Primary Examiner* — Sanjay Cattungal
(74) *Attorney, Agent, or Firm* — Harness, Dickey & Pierce, P.L.C.

(57) ABSTRACT

The apparatus of at least one embodiment includes an input unit, a storage unit, an output unit, and an interface to the imaging device, via which configuration parameters of the imaging device can be read out or transferred. A calculating unit either reads out the configuration parameters from the imaging device or sends the configuration parameters to the imaging device if they have been entered at the input unit by an operator, the configuration parameters being required for the purpose of specifying the quantity of a contrast medium. The calculating unit is so designed as to calculate, on the basis of the parameters that have been entered and/or read out and calculation formulas which are stored in the storage unit, the quantity of a contrast medium that is required for these parameters, and to display the quantity via the output unit.

13 Claims, 2 Drawing Sheets

APPARATUS FOR SPECIFYING THE QUANTITY OF A CONTRAST MEDIUM IN THE CONTEXT OF MEDICAL IMAGING

PRIORITY STATEMENT

The present application hereby claims priority under 35 U.S.C. §119 on German patent application number DE 10 2010 042 931.7 filed Oct. 26, 2010, the entire contents of which are hereby incorporated herein by reference.

FIELD

At least one embodiment of the present invention generally relates to an apparatus for specifying the quantity of a contrast medium in the context of medical imaging, particularly for examinations using computed tomography. The apparatus, in at least one embodiment, can also be used in conjunction with other imaging devices, where the patient has to be injected with a contrast medium during the imaging, e.g. in the context of magnetic resonance tomography.

BACKGROUND

The execution and planning of a CT scan (CT: computed tomography) requires a certain amount of knowledge and experience in order to obtain a satisfactory image result. To an increasing extent, the complex settings of the CT device are performed by the device itself according to examination scenarios that are entered by the operator or scan protocols that are selected by the operator. Partially automated mechanisms are also known, e.g. the automatic or semi-automatic choice of the X-ray voltage.

However, when executing CT scans which involve the injection of a contrast medium, in addition to specifying the configuration parameters of the CT device, it is also necessary to specify the quantity of a contrast medium that is required for the scan.

At present, both the flow of a contrast medium and the quantity of a contrast medium are calculated entirely manually for each patient individually. In many cases, this requires an experienced doctor who is responsible for the calculations relating to the injection of a contrast medium. In other cases, a conservative estimate of the required quantity is usually made, and a sufficient yet generally excessive quantity of a contrast medium is thus administered.

In addition to information that relates directly to the patient, e.g. weight, age, gender, kidney condition, etc., configuration parameters for the CT device are also important in correctly specifying the quantity of a contrast medium. This data is manually included by the operator and used for calculating the quantity of a contrast medium. However, this is demanding and susceptible to error, particularly if the calculation if not performed by a doctor.

SUMMARY

At least one embodiment of the present invention addresses the problem of simplifying the specification of the quantity of a contrast medium in the context of medical imaging for the operator of the imaging device, and reducing the susceptibility to error during the specification.

Advantageous embodiments of the apparatus are the subject matter of the dependent claims or can be derived from the following description and the example embodiments.

At least one embodiment of the apparatus comprises at least an input unit, a storage unit, an interface to the imaging device, a calculating unit and an output unit. Parameters for the imaging examination that is to be executed are entered by an operator via the input unit. According to at least one embodiment of the invention, these can be inter alia or exclusively parameters that are required for calculating the quantity of a contrast medium. They can comprise both patient data, in particular the weight of the patient, and configuration parameters for the imaging device, e.g. the input or selection of a specific scan protocol, the expected duration of the scan, or the selected X-ray voltage for a CT scan. It is also possible to enter the flow of a contrast medium, if this is not automatically calculated by the apparatus.

The storage unit is used to store calculation formulas for calculating the quantity of a contrast medium. It can also be used to store the parameters entered by the operator or data that is received from the imaging device via the interface, e.g. current configuration values and/or parameters or other information.

The interface of the imaging device is designed in such a way that it can be used to read out the current configuration parameters and/or configuration values of the device, or to transfer the desired configuration parameters and/or configuration values to the device.

The calculating unit is designed such that it either retrieves, from the device via the interface, configuration parameters that are required for calculating the quantity of a contrast medium on the basis of the calculation formulas, or—if these configuration parameters have been entered directly at the apparatus by the operator—sends the entered configuration parameters via the interface to the device, which then includes these parameters for the execution of the subsequent imaging examination. In this case, the imaging device is designed in such a way that the configuration parameters can be read out, or received and included, via the aforementioned interface.

Depending on the parameters that have been entered or read out, the calculating unit then invokes the correct calculation formula and uses this calculation formula to calculate the quantity of a contrast medium on the basis of the parameters that have been entered and/or read out. It is noted in this context that only approximation formulas are normally known for calculating the quantity of a contrast medium, and that these can vary in the field of computed tomography depending on the examined body part and the scan protocol, for example.

The correct calculation formula is therefore identified and invoked by the calculating unit depending on the parameters that are entered for this purpose. The parameter ranges to which they apply are therefore stored for each calculation formula accordingly. The calculated quantity of a contrast medium is forwarded from the calculating unit to the output unit, which is used to display the calculated quantity of a contrast medium to the user. In this case, the output unit can be a screen on which the parameters that are entered and/or retrieved can also be displayed during the input and/or output.

At least one embodiment of the apparatus therefore simplifies the specification by the operator of the quantity of a contrast medium that is required for the imaging examination, wherein the quantity no longer has to be calculated manually by the operator. The required formulas can be stored once in the apparatus by an experienced doctor or technician, and subsequently used by all operators. The execution of an imaging examination is consequently also possible for less experienced operators. As a result of the automatic inclusion or delivery of the configuration parameters for the imaging device, these being entered either at the imaging device or at the apparatus, errors in the manual transfer of said parameters are avoided. The configuration parameters need only be entered once in this case, either at the imaging device itself or at the apparatus, and are available both for calculating the quantity of a contrast medium and for configuring the imaging device.

In an example embodiment of the apparatus for use with a CT device, at least the duration of the planned scan is read out via the interface. The X-ray voltage for the planned scan can optionally also be read out, if this is required for the calculation.

In a further embodiment of at least one embodiment of the apparatus, the input unit is designed such that the operator can enter the required configuration parameters for the imaging device via this input unit. The calculating unit then sends this data to the imaging device, such that a separate input is not longer necessary there. The input data for the imaging device preferably relates to the selection or designation of a specific scan protocol and/or the duration of the scan and/or the X-ray voltage.

In a further advantageous embodiment, the delay of a test bolus is read out from the imaging device via the interface, said delay having been determined previously during the execution of a test bolus on the patient using the imaging device. A test bolus is executed with a limited quantity of a contrast medium and X-ray dose, in order to improve the temporal coordination between injection and recording period on the basis of the knowledge of the temporal development. The delay of the test bolus can play an important part in the calculation of the quantity of a contrast medium.

In a further embodiment, the weight of the patient is calculated automatically by the apparatus or the CT device on the basis of a previously created topogram of the patient. Such a calculation is already known. The weight that is determined as part of this activity is then used for calculating the quantity of a contrast medium. Therefore the operator does not have to enter the weight of the patient separately in this case.

The flow of a contrast medium can either be manually entered by the operator or, in a further advantageous embodiment of the apparatus, also be automatically calculated by the apparatus. Corresponding known calculation formulas are then likewise stored for this purpose. The apparatus can be developed separately from the imaging device and exchange the required data with the imaging device via a cable-based or wireless connection. In an advantageous embodiment, the apparatus is however integrated in the imaging device, wherein the input unit for the configuration parameters of the imaging device can also be the input unit of the proposed apparatus.

BRIEF DESCRIPTION OF THE DRAWINGS

The proposed apparatus is briefly explained again below with reference to example embodiments and in connection with the drawings, in which.

DETAILED DESCRIPTION OF THE EXAMPLE EMBODIMENTS

Figure 1:
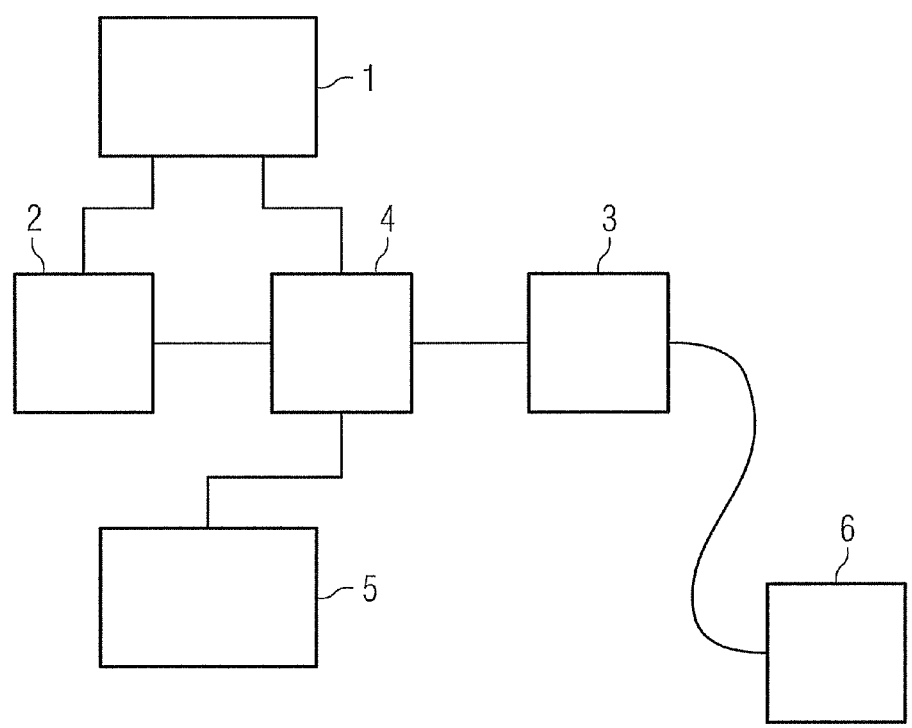
FIG. 1 shows a schematic illustration of the structure of an embodiment of an apparatus.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 schematically shows an example of the underlying structure of an embodiment of the apparatus, which comprises an input unit 1 for the input of examination parameters by an operator of the imaging device, a storage unit 2, an interface 3 to the imaging device 6 (e.g. a CT device), a calculating unit 4 and an output unit 5. The corresponding calculation formulas for calculating the quantity of a contrast medium are stored in the storage unit 2. The apparatus is connected to the CT device 6 via the interface 3, via which configuration parameters of the CT device 6 can be read out or sent to the CT device 6. The calculating unit 4 executes this sending or reading out of the configuration parameters and, on the basis of the configuration parameters that are required for the calculation and other parameters that are entered by the operator, calculates the quantity of a contrast medium and possibly also the flow of a contrast medium.

In a very simple possible embodiment, the following very simple calculation formula may be used for calculating the quantity of a contrast medium in the context of a heart examination. On the basis of a predefined flow of a contrast medium F and an estimated scan duration T that was read out from the CT device, the quantity of a contrast medium is S*T, this being nonetheless at least 60 ml and at most 120 ml. The following formula for calculating the required quantity of a contrast medium C could then be stored in the apparatus as a closed formula in connection with the selected scan protocol for the heart examination:

$$C=\text{MIN}[\text{MAX}[S*T, 60], 120]$$

This value C for the quantity of a contrast medium is then calculated automatically and displayed to the operator.

A possible simple implementation is set forth below with reference to two further examples. Input parameters are used as follows in this context:
 anticipated duration S of the planned scan,
 configured voltage V of the CT device,
 weight W of the patient W (either entered manually or calculated via the topogram),
 a delay D that is specified by a test bolus,
 concentration K of the contrast medium being used, and
 flow of a contrast medium F, wherein this can either be permanently preset or can likewise be specified by way of a formula.

Figure 2:
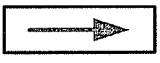
FIG. 2 shows a first example of input parameters and the output of the quantity of a contrast medium.

FIG. 2 shows a first example of possible inputs, formulas and results, wherein the display screen here is used both for showing the inputs at the input unit and possibly configuration parameters that have been read out from the CT device, and as the output unit. In this example, the flow F was entered manually and defined as 5.5 ml/s. The quantity of a contrast medium C which is required for these parameters is then calculated from a formula that is stored in the apparatus.

In this example, the quantity of a contrast medium C is calculated from scan duration S multiplied by the flow, wherein a minimum quantity of 10*F is required, however, and the value is increased by 20 ml if the delay D of the test bolus is greater than 20 s. As a final condition, it is required that no more than 100 ml of contrast medium should be used. The operator enters the corresponding input values if these are not automatically read out from the device. The result is output on the same display page by pressing on a calculation button B. The formulas that are used for the calculation are likewise displayed on the screen in this and in the next example. The quantity M is 24.8 mg in this example.

Figure 3:
FIG. 3 shows a second example of input parameters and the output of the quantity of a contrast medium.

In the second example as per FIG. 3, the flow of a contrast medium F is also calculated from the formula shown on the display screen depending on the weight W of the patient. Furthermore, other values were also changed here, in particular the scan duration S, the delay D and the concentration K of the contrast medium.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An apparatus for specifying a quantity of a contrast medium in the context of medical imaging, comprising:
    an input unit, by which parameters are enterable by an operator for an imaging examination that is to be executed;
    a storage unit, on which are stored at least calculation formulas for specifying the quantity of a contrast medium that is required for the examination;
    an interface to an imaging device, via which configuration parameters of the device can be read out from the device or sent to the device;
    a calculating unit, designed such that it either retrieves from the device via the interface those configuration parameters that are required for a calculation, or sends to the device via the interface those configuration parameters that have been entered and, depending on the parameters that have been at least one entered and read out, invokes the associated calculation formula and uses this calculation formula to calculate the quantity of a contrast medium on the basis of the parameters that have been at least one of entered and read out; and
    an output unit, by which the quantity of a contrast medium that has been calculated by the calculating unit is displayed.

2. The apparatus as claimed in claim 1, wherein the interface is designed for the purpose of communication with a CT device as an imaging device, and the calculating unit is designed such that it reads out from the device via the interface a scan duration that is planned for the imaging examination.

3. The apparatus as claimed in claim 2, wherein the calculating unit is designed such that it reads out via the interface an X-ray voltage that has been set for the imaging examination at the device.

4. The apparatus as claimed in claim 1, wherein the calculating unit is designed such that it transfers to the device, via the interface, configuration parameters for the device that have been entered via the input unit.

5. The apparatus as claimed in claim 1, wherein the calculating unit is designed such that it reads out from the device via the interface a test bolus delay that has been specified by the device.

6. The apparatus as claimed in claim 1, wherein the calculating unit is designed such that it reads out via the interface a weight of a patient to be examined, said weight having been specified by the device on the basis of a topogram.

7. The apparatus as claimed in claim 1, wherein the calculating unit is designed such that it calculates a flow of a contrast medium for the imaging examination that is to be executed.

8. A computed tomograph featuring an apparatus as claimed in claim 1.

9. The apparatus as claimed in claim 1, wherein the apparatus for specifying a quantity of a contrast medium in the context of medical imaging for examinations using computed tomography.

10. The apparatus as claimed in claim 1, wherein the configuration parameters for the device are those that have been entered via at least one of a scan protocol, a scan duration and an X-ray voltage in the case of a planned CT scan.

11. A computed tomograph featuring an apparatus as claimed in claim 2.

12. A computed tomograph featuring an apparatus as claimed in claim 3.

13. The apparatus as claimed in claim 2, wherein the configuration parameters for the device are those that have been entered via at least one of a scan protocol, a scan duration and an X-ray voltage in the case of a planned CT scan.

* * * * *